(12) United States Patent
Ichihara et al.

(10) Patent No.: US 6,455,726 B2
(45) Date of Patent: Sep. 24, 2002

(54) MANUFACTURING METHOD

(75) Inventors: Masaharu Ichihara, Mino; Norio Hashimoto, Ibaraki; Atsushi Kanda, Ikeda; Kooji Kagara, Mino, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/782,291

(22) Filed: Feb. 14, 2001

Related U.S. Application Data

(62) Division of application No. 09/446,359, filed as application No. PCT/JP98/02612 on Jun. 15, 1998, now Pat. No. 6,291,680.

(30) Foreign Application Priority Data

Jun. 18, 1997 (JP) ............................................. 9-160806

(51) Int. Cl.$^7$ ............................................. C07C 229/00
(52) U.S. Cl. ........................ 560/39; 562/444; 562/565; 560/170
(58) Field of Search ................. 560/39, 170; 562/444, 562/565

(56) References Cited

FOREIGN PATENT DOCUMENTS

| GB | 2095659 | * | 10/1982 |
| WO | WO-9611210 | * | 4/1996 |

OTHER PUBLICATIONS

T. Bandiera, et al., "On the Oximation of Diaryl–β–diketones", J. Heterocyclic Chem., vol. 29, pp. 1423–1428, Oct.–Nov. 1992.

* cited by examiner

Primary Examiner—Alan L. Rotman
Assistant Examiner—Binta Robinson
(74) Attorney, Agent, or Firm—Oblon, Spivak, McClelland, Maier & Neustadt, P.C.

(57) ABSTRACT

A compound of the following formula (II) and a process for preparing of the compound of the following formula (I) its preparation (I)

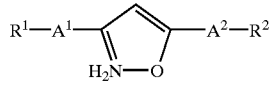

wherein $R^1$ is carboxy or protected carboxy;

$R^2$ is lower alkoxy or higher alkoxy;

$A^1$ is a divalent aromatic ring, a divalent heterocyclic group or a divalent cyclo(lower)alkane; and $A^2$ is a divalent aromatic ring, a divalent heterocyclic group or a divalent cyclo(lower)alkane, or a salt thereof. The process comprises, reacting a compound of the formula (III):

(III)

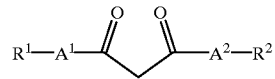

wherein $R^1$, $R^2$, $A^1$ and $A^2$ are each as defined above or a salt thereof, with an acid ammonium salt to give a compound of the formula (II).

6 Claims, No Drawings

MANUFACTURING METHOD

This application is a Divisional of 09/446,359, filed Dec. 20, 1999, now U.S. Pat. No. 6,291,680, which is a 371 of application Ser. No. PCT/JP98/02612, filed Jun. 15, 1998.

TECHNICAL FIELD

The present invention relates to a process for preparing a compound which is useful as a starting material for the manufacture of an excellent antifungal agent whereby it is useful in the field of pharmaceutical industry.

BACKGROUND ART

In the International Laid-Open Gazette WO 96/11210, there is a disclosure on a method wherein 1-(4-methoxycarbonylphenyl)-3-(4-pentyloxyphenyl)propane-1,3-dione which is a starting material for the synthesis of antifungal agents of lipopeptide type is made to react with hydroxylamine hydrochloride to give methyl 4-[5-(4-pentyloxyphenyl)-isoxazol-3-yl]benzoate which is an aimed compound.

DISCLOSURE OF THE INVENTION

In the method mentioned in the above international patent application, 1-(4-methoxycarbonylphenyl)-3-(4-pentyloxyphenyl)propane-1,3-dione which is a starting material is made to react with hydroxylamine hydrochloride whereupon the aimed methyl 4-[5-(4-pentyloxyphenyl)-isoxazol- 3-yl]benzoate is prepared. However, besides the aimed compound, its isomers are contaminated therein and, since separation of the aimed compound from the isomers is difficult, the yield of the aimed methyl 4-[5-(4-pentyloxyphenyl)isoxazol-3-yl]benzoate is not fully satisfactory.

In view of the above, the present inventors have carried out an intensive investigation and, as a result, they have found a manufacturing method in which isomers of methyl 4-[5-(4-pentyloxyphenyl)isoxazol-3-yl]benzoate are not produced whereby the above-mentioned problem in the conventional method has been solved. They have found a method for the manufacture of the related compounds as well.

The manufacturing method according to the present invention may be shown by the following reaction formulae.

Step 1

$R^1—A^1$—(structure)—$A^2—R^2$ $\xrightarrow{\text{acid ammonium salt}}$ (III) or a salt thereof $R^1—A^1$—(structure with $H_2N$)—$A^2—R^2$ (II) or a salt thereof

[Wherein
R$^1$ is carboxy or protected carboxy;
R$^2$ is lower alkoxy or higher alkoxy;
A$^1$ is divalent aromatic ring, divalent heterocyclic group or divalent cyclo(lower)alkane; and
A$^2$ is divalent aromatic ring, divalent heterocyclic group or divalent cyclo(lower)alkane.]

Step 2

$R^1—A^1$—(structure with $H_2N$)—$A^2—R^2$ $\xrightarrow{\text{NH}_2\text{OH or a salt thereof}}$ (II) or a salt thereof $R^1—A^1$—(isoxazole)—$A^2—R^2$ (I) or a salt thereof

[Wherein
R$^1$ is carboxy or protected carboxy;
R$^2$ is lower alkoxy or higher alkoxy;
A$^1$ is divalent aromatic ring, divalent heterocyclic group or divalent cyclo (lower) alkane; and
A$^2$ is divalent aromatic ring, divalent heterocyclic group or divalent cyclo (lower) alkane.]

The characteristic feature of this manufacturing method is to carry out the reaction through the compound (II) or a salt from the starting compound (III) or a salt, and the said compound (II) or a salt is novel.

An preferable salt of the compounds (I), (II) and (III) is a conventional nontoxic mono- or di-salt, and its examples are metal salt such as alkaline metal salt (e.g., sodium salt, potassium salt, etc.) and alkaline earth metal salt (e.g., calcium salt, magnesium salt, etc.); ammonium salt; salt with an organic base (e.g., trimethylamine salt, triethylamine salt, pyridine salt, picoline salt, dicyclohexylamine salt, N,N'-dibenzylethylenediamine salt, etc.); addition salt with an organic acid (e.g., formate, acetate, trifluoroacetate, maleate, tartrate, methanesulfonate, benzenesulfonate, toluenesulfonate, etc.); addition salt with an inorganic acid (e.g., hydrochloride, hydrobromide, hydroiodide, sulfate, phosphate, etc.); salt with an amino acid (e.g., arginine, aspartic acid, glutamic acid, etc.); etc.

Suitable examples and explanations for various definitions included within the scope of the present invention mentioned in this specification both hereinabove and hereinafter will be mentioned in detail as follows.

Unless otherwise provided, "lower" is used to intend a group having 1 to 6 carbon atom(s).

Unless otherwise provided, "higher" is used to intend a group having 7 to 20 carbon atoms.

Suitable "lower alkoxy" may include straight or branched chain such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, and the like. More preferably, it is ($C_3$–$C_5$) alkoxy and, most preferably, it is pentyloxy.

Suitable "higher alkoxy" may include straight or branched chain such as heptyloxy, octyloxy, 5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, eicosyloxy, and the like.

Suitable "divalent aromatic ring" may include divalent group derived from benzene which may have lower alkyl (e.g., benzene, toluene, mesitylene, etc.), naphthalene, anthracene, etc., and more preferably, it is phenylene.

Suitable "divalent heterocyclic group" may include divalent group which is derived from:

unsaturated 3 to 8-membered (more preferably, 5 or 6-membered) heteromonocyclic group containing 1 to 4 nitrogen atom(s), for example, pyrroline, imidazole, pyrazole, pyridine, dihydropyridine, pyrimidine, pirazine, pyridazine, triazole (e.g., 4H-1,2,4-triazole, 1H-1,2,3-triazole, 2H-1,2,3 -triazole, etc.), tetrazole (e.g., 1H-tetrazole, 2H-tetrazole, etc.), etc.;

saturated 3 to 8-membered (more preferably, 5 or 6-membered) heteromonocyclic group containing 1 to 4 nitrogen atom(s), for example, pyrrolidine, piperidine, piperazine, etc.;

unsaturated condensed heterocyclic group containing 1 to 4 nitrogen atom(s), for example, indole, isoindole, indolizine, benzoimidazole, quinoline, dihydroquinoline, isoquinoline, indazole, quinoxaline, dihydroquinoxaline, benzotriazole, etc.;

unsaturated 3 to 8-membered (more preferably, 5 or 6-membered) heteromonocyclic group containing 1 or 2 oxygen atom(s) and 1 to 3 nitrogen atom(s), for example, oxazole, isoxazole, oxadiazole (e.g., 1,2,4-oxadiazole, 1,3,4-oxadiazole, 1,2,5-oxadiazole, etc.), etc.;

saturated 3 to 8-membered (more preferably, 5 or 6-membered) heteromonocyclic group containing 1 or 2 oxygen atom(s) and 1 to 3 nitrogen atom(s), for example, morpholine, sydnone, etc.;

unsaturated condensed heterocyclic group containing 1 or 2 oxygen atom(s) and 1 to 3 nitrogen atom(s), for example, benzoxazole, benzoxadiazole, etc.;

unsaturated 3 to 8-membered (more preferably, 5 or 6-membered) heteromonocyclic group containing 1 or 2 sulfur atom(s) and 1 to 3 nitrogen atom(s), for example, thiazole, isothiazole, thiadiazole (e.g., 1,2,3-thiadiazole, 1,2,4-thiadiazole, 1,3,4-thiadiazole, 1,2,5-thiadiazole, etc.), dihydrothiadiazole, etc.;

saturated 3 to 8-membered (more preferably, 5 or 6-membered) heteromonocyclic group containing 1 or 2 sulfur atom(s) and 1 to 3 nitrogen atom(s), for example, thiazolidine, etc.;

unsaturated 3 to 8-membered (more preferably, 5 or 6-membered) heteromonocyclic group containing 1 or 2 sulfur atom(s), for example, thiophene, dihydrothiophene, dihydrodithiophene, etc.;

unsaturated condensed heterocyclic group containing 1 or 2 sulfur atom(s) and 1 to 3 nitrogen atom(s), for example, benzothiazole, benzothiadiazole, etc.;

unsaturated 3 to 8-membered (more preferably, 5 or 6-membered) heteromonocyclic group containing one oxygen atom, for example, furan, etc.;

unsaturated 3 to 8-membered (more preferably, 5 or 6-membered) heteromonocyclic group containing one oxygen atom and 1 or 2 sulfur atom(s), for example, dihydroxathiophene, etc.;

unsaturated condensed heterocyclic group containing 1 or 2 sulfur atom(s), for example, benzothiophene, benzodithiophene, etc.; and unsaturated condensed heterocyclic group containing one oxygen atom and 1 or 2 sulfur atom(s), for example, benzoxathiophene, etc.

Suitable "divalent cyclo(lower)alkane" may include divalent group derived from cyclopropane, cyclobutane, cyclopentane, cyclohexane, etc.

Suitable "protected carboxy" may include a common one such as an esterified carboxy, and specific examples of the ester moiety in the said esterified carboxy are:

lower alkyl ester [e.g., methyl ester, ethyl ester, propyl ester, isopropyl ester, butyl ester, isobutyl ester, tert-butyl ester, pentyl ester, hexyl ester, 1-cyclopropylethyl ester, etc.], suitably substituted lower alkyl ester, for example, lower alkanoyloxy lower alkyl ester [e.g., acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxyethyl ester, 2-propionyloxyethyl ester, hexanoyloxymethyl ester, etc.], lower alkanesulfonyl lower alkyl ester [e.g., 2-mesylethyl ester, etc.] or mono-(or di- or tri-)halo lower alkyl ester [e.g., 2-iodoethyl ester, 2,2,2-trichloroethyl ester, etc.], etc.;

higher alkyl ester [e.g., heptyl ester, octyl ester, 3,5-dimethyloctylester, 3,7-dimethyloctyl ester, nonyl ester, decyl ester, undecyl ester, dodecyl ester, tridecyl ester, tetradecyl ester, pentadecyl ester, hexadecyl ester, heptadecyl ester, octadecyl ester, nonadecyl ester, adamantyl ester, etc.];

lower alkenyl ester [e.g., $C_2$–$C_6$ alkenyl ester (e.g., vinyl ester, allyl ester, etc.)];

lower alkynyl ester [e.g., $C_2$–$C_6$ alkynyl ester (e.g., ethynyl ester, propynyl ester, etc.)];

aryl lower alkyl ester which may have one or more suitable substituent(s) [e.g., phenyl lower alkyl ester which may have 1 to 4 lower alkoxy, halogen, nitro, hydroxyl, lower alkyl, phenyl or halo lower alkyl (e.g., benzyl ester, 4-methoxybenzyl ester, 4-chlorobenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, 4-trifluoromethylbenzyl ester, etc.), etc.];

aryl ester which may have one or more suitable substituent(s) [e.g., aryl ester which may have 1 to 4 lower alkyl or halogen (e.g., phenyl ester, 4-chlorophenyl ester, tolyl ester, 4-tert-butylphenyl ester, xylyl ester, mesityl ester, cumenyl ester, etc.), etc.];

cycloalkyloxycarbonyloxy lower alkyl ester which may have lower alkyl [e.g., cyclopentyloxycarbonyloxymethyl ester, cyclohexyloxycarbonyloxymethyl ester, cycloheptyloxycarbonyloxymethyl ester, 1-methylcyclohexyloxycarbonyloxymethyl ester, 1-(or 2-)[cyclopentyloxycarbonyloxy]ethyl ester, 1-(or 2-)[cyclohexyloxycarbonyloxy]ethyl ester, 1-(or 2-)[cycloheptyloxycarbonyloxy]ethyl ester, etc.]; and (5-lower alkyl-2-oxo-1,3-dioxol-4-yl) lower alkyl ester [e.g., (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)methyl ester, 1-(or 2-)(5-methyl-2-oxo-1,3-dioxol-4-yl)ethyl ester, 1-(or 2-)(5-ethyl-2-oxo-1,3-dioxol-4-yl)ethyl ester, 1-(or 2-)(5-proyl-2-oxo-1,3-dioxol-4-yl)ethyl ester, etc.], etc.

and, among them, preferred ones are lower alkyl ester, lower alkanoyloxy lower alkyl ester, aryl lower alkyl ester which may have one or more suitable substituent (s), cycloalkyloxycarbonyloxy lower alkyl ester which may have lower alkyl, higher alkyl ester and (5-lower alkyl-2-oxo-1,3-dioxol-4-yl)lower alkyl ester; more preferred one is lower alkyl ester; and most preferred one is methyl ester.

A preferred embodiment of the present invention is a manufacturing method in which the starting compound (III) is wherein $R^1$ is lower alkoxycarbonyl, $R^2$ is lower alkoxy, $A^1$ is divalent aromatic ring and
$A^2$ is divalent aromatic ring,
and most preferred embodiment thereof is that
where
$R^1$ is methoxycarbonyl,
$R^2$ is pentyloxy,
$A^1$ is phenylene and
$A^2$ is phenylene.

Manufacturing method in accordance with the present invention will now be illustrated in detail as follows.

Step 1:

A compound (II) or a salt thereof can be manufactured by the reaction of a compound (III) or a salt thereof with an acid ammonium salt such as ammonium acetate, ammonium carbonate or ammonium formate.

This reaction is usually carried out in a solvent which does not affect the reaction such as water, alcohol (e.g., methanol, ethanol, propanol, etc.), benzene, N,N-dimethylformamide, dimethyl sulfoxide, tetrahydrofuran, toluene, methylene chloride, ethylene dichloride, chloroform, 1,2-dimethoxyethane, dioxane, ethyl acetate, diethyl ether or a mixture thereof.

Although there is no particular limitation for the reaction temperature, the reaction is usually carried out at room temperature or with warming or heating. The temperature is preferably 60 to 120° C. or, more preferably, 90 to 100° C.

Step 2:

A compound (I) or a salt thereof can be manufactured by the reaction of a compound (II) or a salt thereof with hydroxylamine or a salt thereof.

This reaction is usually carried out in a solvent which does not affect the reaction such as water, alcohol (e.g., methanol, ethanol, propanol, etc.), benzene, N,N-dimethylformamide, dimethyl sulfoxide, tetrahydrofuran, toluene, methylene chloride, methylene dichloride, chloroform, 1,2-dimethoxyethane, dioxane, ethyl acetate, diethyl ether or a mixture thereof.

Although there is no particular limitation for the reaction temperature, the reaction is usually carried out at room temperature or with warming or heating. The temperature is preferably 50 to 100° C. or, more preferably, 55 to 60° C.

The compounds (I) and (II) obtained according to the manufacturing method of the present invention can be separated and purified by common means such as disintegration, recrystallization, column chromatography or re-precipitation.

The compounds (I) and (II) obtained according to the manufacturing method of the present invention may contain one or more stereoisomer(s) such as geometrical isomer and optical isomers due to asymmetric carbon and double bond, and a method for the manufacture of such an isomer and a mixture thereof is also within a scope of the present invention.

In the known manufacturing method (WO 96/11210), an isomer of the aimed methyl 4-[5-(4-pentyloxyphenyl)-isoxazol-3-yl]benzoate was produced as a by-product, and separation of the aimed compound from this isomer was difficult.

No isomer for the aimed compound is produced from the compound (II) which is prepared according to the manufacturing method of the present invention and, therefore, purification of the aimed compound is easy, and the aimed compound having a high purity can be obtained in a high yield whereby the present invention is useful as a manufacturing method in an industrial scale.

Incidentally, the starting compound (III) can be easily manufactured from a less expensive compound and, accordingly, the present invention is advantageous in terms of cost as well.

EXAMPLES

The present invention will now be specifically illustrated by the following examples.

Preparation 1 p-Hydroxyacetophenone (40.0 g), n-pentyl bromide (48.8 g) and dimethylformamide (200 ml) were charged in 1-liter three-necked flask, and disintegrated potassium carbonate (48.7 g) was added thereto with stirring. The mixture was heated, and the reaction was carried out for 3 hours at the inner temperature of 65 to 70° C. After completion of the reaction, the mixture was cooled, water (360 ml) and n-heptane (360 ml) were added thereto and, after the mixture was stirred, it was separated to collect a n-heptane layer. The n-heptane layer was washed with 0.5N aqueous solution (200 ml) of sodium hydroxide twice and, finally, washed with a saturated saline solution (200 ml). The n-heptane solution was concentrated in vacuo to give p-pentyloxyacetophenone (64.0 g).

NMR(CDCl$_3$, δ): 0.94(3H, t, J=1.4 Hz), 1.35–1.53(4H, m), 1.73–1.88(2H, m), 2.55(3H, s), 4.01(2H, t, J=1.3 Hz), 6.91(2H, d, J=1.8 Hz), 7.92(2H, d, J=1.8 Hz)

MASS(m/z): 207(M+H$^+$)

Preparation 2

Dimethylformamide (600 ml), p-pentyloxyacetophenone (60.0 g) and dimethyl terephthalate (73.5 g) were charged in 1-liter three-necked flask and stirred. To this mixture was added 28% methanolic solution (84.2 g) of sodium methoxide and, after that, a reaction was carried out at the inner temperature of 35 to 40° C. for 48 hours. After completion of the reaction, the reaction solution was added to a mixed solution of water (3,000 ml) and 1N hydrochloric acid (600 ml) to separate the crystals. The mixture was stirred at room temperature for 1 hour, and then the separated crystals were filtered. The wet crystals and methanol (1,000 ml) were charged in a 2-liter three-necked flask, heated to reflux for 2 hours and cooled down to room temperature, and the crystals were filtered. The crystals were washed with methanol (200 ml). The crystals were dried overnight in vacuo to give 1-(4-methoxycarbonylphenyl)-3-(4-pentyloxyphenyl)-propane-1,3-dione (66.0 g).

NMR(CDCl$_3$, δ): 0.95(3H, t, J=1.4 Hz), 1.30–1.60(4H, m), 1.76–1.89(2H, m), 3.95(3H, s), 4.03(2H, t, J=1.3 Hz), 6.84(1H, s), 6.98(2H, d, J=1.4 Hz), 7.99(2H, d, J=1.4 Hz), 8.01(2H, d, J=1.7 Hz), 8.13(2H, d, J=1.7 Hz)

MASS(m/z): 369(M+H$^+$)

Example 1

Dimethylformamide (50 ml), 1-(4-methoxycarbonylphenyl)-3-(4-pentyloxyphenyl)propane-1,3-dione (10.0 g) and ammonium acetate (9.9 g) were charged in 500-ml three-necked flask at room temperature and heated, and the reaction was carried out at the inner temperature of 90 to 100° C. for 4 hours. After completion of the reaction, the mixture was cooled down to room temperature, water (250 ml) and ethyl acetate (250 ml) were added, the mixture was stirred, and an ethyl acetate layer was separated. The ethyl acetate layer was further washed with water (250 ml) and a saturated saline solution (100 ml). The ethyl acetate layer was concentrated in vacuo to make 50 ml, and n-heptane (250 ml) was added to separate crystals of 1-amino-1-(4-methoxycarbonylphenyl)-3-oxo-3-(4-pentyloxyphenyl)-1-propene. The crystals were filtered at room temperature and washed with a solution (50 ml)

consisting of n-heptane and ethyl acetate (5:1). The crystals were dried overnight in vacuo and purified by suspending in a 70% aqueous acetone (100 ml) to give 1-amino-1-(4-methoxycarbonylphenyl)-3-oxo-3-(4-pentyloxyphenyl)-1-propene (6.56 g).

NMR(CDCl$_3$, δ): 0.94(3H, t, J=1.4 Hz), 1.30–1.55(4H, m), 1.70–1.90(2H, m), 3.96(3H, s), 4.01(2H, t, J=1.3 Hz), 6.13(1H, brs), 6.92(2H, d, J=1.8 Hz), 7.70(2H, d, J=1.7 Hz), 7.92(2H, d, J=1.8 Hz), 8.13(2H, d, J=1.7 Hz)

MASS (m/z): 368 (M+H$^+$)

Example 2

Dimethylformamide (44 ml), 1-amino-1-(4-methoxycarbonylphenyl)-3-oxo-3-(4-pentyloxyphenyl)-1-propene (5.5 g) and hydroxylamine hydrochloride (2.0 g) were charged in 300-ml three-necked flask at room temperature and heated, and the reaction was carried out at the inner temperature of 55 to 60° C. for 4 hours. After completion of the reaction, the mixture was cooled down to room temperature, and acetonitrile (110 ml) was added to separate the crystals. The inner temperature was made 0 to 5° C., and the crystals were filtered and washed with acetonitrile (28 ml) and water (110 ml). The crystals were dried overnight in vacuo to give methyl 4-[5-(4-pentyloxyphenyl)isoxazol-3-yl]benzoate (5.21 g)

NMR(CDCl$_3$, δ): 0.95(3H, t, J=1.4 Hz), 1.30–1.60(4H, m), 1.75–1.92(2H, m), 3.95(3H, s), 4.01(2H, t, J=1.3 Hz), 6.74(1H, s), 6.99(2H, d, J=1.8 Hz), 7.76(2H, d, J=1.7 Hz), 7.93(2H, d, J=1.7 Hz), 8.14(2H, d, J=1.7 Hz)

MASS(m/z): 366(M+H$^+$)

What is claimed is:

1. A process for preparing a compound of the formula (II)

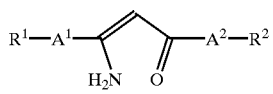
(II)

wherein
   $R^1$ is a carboxy group or a protected carboxy;
   $R^2$ is a lower alkoxy or a higher alkoxy;
   $A^1$ is a divalent aromatic ring or a divalent cyclo(lower)alkane; and
   $A^2$ is a divalent aromatic ring or a divalent cyclo(lower)alkane
or a salt thereof, said process comprises,
reacting a compound of the formula (III):

(III)

wherein $R^1$, $R^2$, $A^1$ and $A^2$ are each as defined above or a salt thereof, with an acid ammonium salt.

2. The process of claim 1, wherein
   $R^1$ is a protected carboxy,
   $R^2$ is a lower alkoxy,
   $A^1$ is a divalent aromatic ring and
   $A^2$ is a divalent aromatic ring.

3. The process of claim 2, wherein
   $A^1$ is a divalent aromatic ring, and
   $A^2$ is divalent aromatic ring.

4. The process of claim 3, wherein
   $A^1$ is phenylene, and
   $A^2$ is phenylene.

5. A compound of the formula (II):

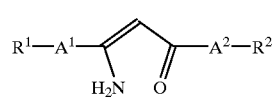
(II)

wherein
   $R^1$ is a carboxy or a protected carboxy;
   $R^2$ is a lower alkoxy or a higher alkoxy;
   $A^1$ is a divalent aromatic ring or a divalent cyclo(lower)alkane; and
   $A^2$ is a divalent aromatic ring or a divalent cyclo(lower)alkane
or a salt thereof.

6. A process for preparing a compound of the formula (II)

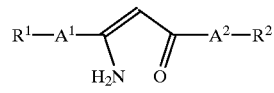
(II)

wherein
   $R^1$ is a carboxy methyl;
   $R^2$ is a pentyloxy;
   $A^1$ is a phenyl; and
   $A^2$ is a phenyl;
or a salt thereof, said process comprising:
   reacting a compound of the formula (III):

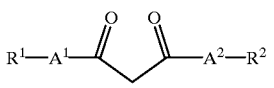
(III)

wherein $R^1$, $R^2$, $A^1$ and $A^2$ are each as defined above or a salt thereof, with an acid ammonium salt.

* * * * *